(12) United States Patent
Putha et al.

(10) Patent No.: US 11,636,596 B1
(45) Date of Patent: Apr. 25, 2023

(54) MONITORING BRAIN CT SCAN IMAGE (71) Applicant: Qure.ai Technologies Private Limited, Mumbai (IN)

(72) Inventors: Preetham Putha, Vijayawada (IN); Sasank Chilamkurthy, Vijayawada (IN); Satish Kumar Golla, Gadwal (IN); Swetha Tanamala, Vijayawada (IN); Ujjwal Upadhyay, Noida (IN)

(73) Assignee: Qure.ai Technologies Private Limited, Mumbai (IN)

( * ) Notice: Subject to any disclaimer, the term of this patent is extended or adjusted under 35 U.S.C. 154(b) by 0 days.

(21) Appl. No.: 17/986,066

(22) Filed: Nov. 14, 2022

Related U.S. Application Data (63) Continuation-in-part of application No. 17/858,191, filed on Jul. 6, 2022, now Pat. No. 11,501,437.

(30) Foreign Application Priority Data

Apr. 28, 2022 (IN) .............................. 202221025072

(51) Int. Cl.
*G06T 7/00* (2017.01)
*G06T 3/40* (2006.01)
(Continued)

(52) U.S. Cl.
CPC .......... *G06T 7/0012* (2013.01); *G06T 3/4007* (2013.01); *G06T 5/10* (2013.01);
(Continued)

(58) Field of Classification Search
CPC ........ G16H 50/20; G16H 50/30; G16H 30/40; G06V 2201/03; G06T 7/0012; G06T 7/11; G06T 2207/10081; G06T 2207/30016
See application file for complete search history.

(56) References Cited

U.S. PATENT DOCUMENTS 10,475,182 B1 * 11/2019 Chilamkurhy ...... G06F 18/2433
10,898,152 B1 * 1/2021 Kim ..................... A61B 6/5217
(Continued)

FOREIGN PATENT DOCUMENTS

CN    112862022 A    5/2021
JP      6906462 B2   7/2021
(Continued)

OTHER PUBLICATIONS

Philip A Barber, Andrew M Demchuk, Jinjin Zhang, Alastair M Buchan, Validity and reliability of a quantitative computed tomography score in predicting outcome of hyperacute stroke before thrombolytic therapy, The Lancet, vol. 355, Issue 9216, 2000, pp. 1670-1674, (Year: 2000).

(Continued)

*Primary Examiner* — Gandhi Thirugnanam
(74) *Attorney, Agent, or Firm* — Shumaker, Loop & Kendrick, LLP (57) ABSTRACT

A system and a method for monitoring a brain CT scan image using ASPECTS score. The method includes receiving the brain CT scan image of a patient. Further, a basal ganglia region and a corona radiata level are identified in a plurality of slices in the brain CT scan image. Furthermore, a plurality of anatomical regions, a plurality of infarcts and a plurality of black regions are segmented using deep learning. Subsequently, an overlapping region across the plurality of slices is determined based on the plurality of anatomical regions, the plurality of infarcts, and the plurality of black regions. The overlapping region and a predefined threshold are used to compute an ASPECTS score. The ASPECTS score is further used to recommend a course of action to the patient.

13 Claims, 5 Drawing Sheets

(51) Int. Cl.
*G06T 5/10* (2006.01)
*G06T 7/11* (2017.01)
*G16H 50/20* (2018.01)
*G06V 10/25* (2022.01)

(52) U.S. Cl.
CPC ............. *G06T 7/11* (2017.01); *G06V 10/25* (2022.01); *G16H 50/20* (2018.01); *G06T 2207/10081* (2013.01); *G06T 2207/20056* (2013.01); *G06T 2207/30016* (2013.01); *G06V 2201/07* (2022.01)

(56) References Cited

U.S. PATENT DOCUMENTS

| | | | |
|---|---|---|---|
| 10,950,337 B1* | 3/2021 | Shin | A61B 6/00 |
| 11,263,749 B1* | 3/2022 | Purushottam | G16H 10/60 |
| 11,278,260 B1* | 3/2022 | Putha | A61B 8/463 |
| 11,501,437 B1* | 11/2022 | Upadhyay | G16H 30/40 |
| 2015/0012466 A1* | 1/2015 | Sapiro | A61B 6/501 706/12 |
| 2016/0157800 A1* | 6/2016 | Goyal | A61B 6/486 600/431 |
| 2019/0122236 A1 | 4/2019 | Greveson | |
| 2019/0122363 A1* | 4/2019 | Greveson | G06T 7/37 |
| 2020/0066393 A1* | 2/2020 | Kaiser | G06N 3/047 |
| 2020/0258226 A1* | 8/2020 | Nakamura | G16H 40/20 |
| 2020/0294241 A1* | 9/2020 | Wu | G06T 7/11 |
| 2021/0098115 A1* | 4/2021 | Shin | G06T 5/002 |
| 2021/0142480 A1* | 5/2021 | Thomson | G16H 50/20 |
| 2022/0020152 A1* | 1/2022 | Orasanu | G06T 7/0014 |
| 2022/0115136 A1* | 4/2022 | Fuchigami | G06N 3/08 |

FOREIGN PATENT DOCUMENTS

| | | |
|---|---|---|
| JP | 2021183113 A | 12/2021 |
| KR | 101992057 B1 | 6/2019 |
| KR | 102189622 B1 | 12/2020 |

OTHER PUBLICATIONS

Jung, Su-Min & Whangbo, Teag Keun. (2018). Evaluating a Deep-Learning System for Automatically Calculating the Stroke ASPECT Score. 564-567, (Year: 2018).

Takuya Fuchigami, Sadato Akahori, Takayuki Okatani, Yuanzhong Li, "A hyperacute stroke segmentation method using 3D U-Net integrated with physicians' knowledge for NCCT," Proc. SPIE 11314, Medical Imaging 2020: Computer-Aided Diagnosis, 113140G (Mar. 16, 2020), (Year: 2010).

Tan, C. et al., "DeepBrainSeg: Automated Brain Region Segmentation for Micro-Optical Images With a Convolutional Neural Network", Front. Neurosci., Mar. 20, 2020, Sec. Brain Imaging Methods, p. 1-13 (Year: 2020).

* cited by examiner

MONITORING BRAIN CT SCAN IMAGE

PRIORITY INFORMATION

The present application is a continuation-in-part claiming a priority from the parent application U.S. Pat. No. 17/858,191 FILED Jul. 6, 2022.

TECHNICAL FIELD

The present subject matter described herein, in general, relates to a system and a method for monitoring a brain CT scan image. More particularly, to monitoring the brain CT scan image using an ASPECTS score.

BACKGROUND

Typically, a stroke occurs when an artery in brain ruptures and bleeds or when the blood supply to the brain is cut off. Blood and oxygen cannot reach the brain's tissues due to the rupture or obstruction, resulting in tissue death. The Middle Cerebral Artery (MCA) is the largest cerebral artery and the most commonly damaged vessel in stroke. The quick onset of a focused neurological deficit caused by interruption of blood flow in the territory supplied by the MCA is known as an MCA stroke. Alberta Stroke Program Early CT Score (ASPECTS) is used to estimate the extent of early ischemic changes in patients with MCA stroke.

Generally, ASPECTS is done by a radiologist, for a patient with potential signs of stroke. However, in Low Middle Income Countries (LMICs), there may be hospitals where radiologists are not available and general physicians may have to take cases and recommend those to the right doctor. Also, existing techniques used to analyze the ASPECTS needs human intervention, and thus it may lead to an error in the analysis. In case of any such error, the doctor may recommend wrong treatment to a patient. Therefore, there is a need for an improved method and system for an automatic and accurate analysis of the ASPECTS.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for monitoring a brain CT scan image using an Alberta Stroke Programme Early CT Score (ASPECTS) score. This summary is not intended to identify essential features of the claimed subject matter nor is it intended for use in determining or limiting the scope of the claimed subject matter.

In one implementation, a method for monitoring a brain CT scan image using an ASPECTS score is disclosed. Initially, a brain CT scan image of a patient may be received. Further, the brain CT scan image may be resampled into a plurality of slices. In one aspect, the brain CT scan image may be resampled using a bilinear interploration. Subsequently, a basal ganglia region and a corona radiata level may be identified in the plurality of slices. The basal ganglia region and the corona radiata level may be identified in a Middle Cerebral Artery (MCA) territory using a deep learning model. Upon identification of the basal ganglia region and the corona radiata level, a plurality of anatomical regions may be segmented. The plurality of anatomical regions may be segmented using deep learning. The plurality of anatomical regions may be segmented on a set of slices associated with the basal ganglia region and the corona radiata level. Further, a plurality of infarcts may be segmented in the plurality of slices using the deep learning model. Furthermore, a white matter region and a grey matter region in the plurality of slices may be extracted using a windowing technique. Upon extraction, a density of the white matter region and a density of the grey matter region on each of the plurality of slices may be determined based on an analysis of the plurality of slices using a fast Fourier transform technique. Subsequently, a plurality of black regions in the plurality of slices may be segmented based on comparison of the density of the white matter region and the grey matter region with a threshold density.

Further, an overlapping region across the plurality of slices may be determined. The overlapping region may be determined based on the plurality of anatomical regions, the plurality of infarcts, and the plurality of black regions. The overlapping region may indicate an affected area of brain in the brain CT scan image. Once the overlapping region is determined, an ASPECTS score may be computed based on the overlapping region and a predefined threshold. In one aspect, a defined point may be deducted from the predefined threshold when the overlapping region is determined. Finally, a course of action may be recommended to the patient in real-time based on the ASPECTS score and a threshold score, thereby monitoring a brain CT scan image. In one aspect, the aforementioned method for monitoring a brain CT scan image may be performed by a processor using programmed instructions stored in a memory.

In another implementation, a non-transitory computer readable medium embodying a program executable in a computing device for monitoring a brain CT scan image using an ASPECTS score is disclosed. The program may comprise a program code for receiving a brain CT scan image of a patient may be received. Further, the program may comprise a program code for resampling the brain CT scan image into a plurality of slices. In one aspect, the brain CT scan image may be resamoled using a bilinear interpolation. Subsequently, the program may comprise a program code for identifying a basal ganglia region and a corona radiata level in the plurality of slices. The basal ganglia region and the corona radiata level may be identified in a Middle Cerebral Artery (MCA) territory using a deep learning model. The program may further comprise a program code for segmenting a plurality of anatomical regions upon identification of the basal ganglia region and the corona radiata level. The plurality of anatomical regions may be segmented using deep learning. The plurality of anatomical regions may be segmented on a set of slices associated with the basal ganglia region and the corona radiata level. Further, the program may comprise a program code for segmenting a plurality of infarcts in the plurality of slices using the deep learning. Furthermore, the program may comprise a program code for extracting a white matter region and a grey matter region in the plurality of slices using a windowing technique. Upon extraction, the program may comprise a program code for determining a density of the white matter region and a density of the grey matter region on each of the plurality of slices based on an analysis of the plurality of slices using a fast Fourier transform technique. Subsequently, the program may comprise a program code for segmenting a plurality of black regions in the plurality of slices based on comparison of the density of the white matter region and the grey matter region with a threshold density.

The program may further comprise a program code for determining an. overlapping region across the plurality of slices. The overlapping region may be determined based on the plurality of anatomical regions, the plurality of infarcts, and the plurality of black regions. The overlapping region, may indicate an affected area of brain in the brain CT scan image. Subsequently, the program may comprise a program code for computing an ASPECTS score based on the overlapping region and a predefined threshold. In one aspect, a defined point may be deducted from the predefined threshold when the overlapping region is determined. Finally, the program may comprise a program code for recommending a course of action to the patient in real-time based on the ASPECTS score and a threshold score, thereby monitoring a brain CT scan image.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for monitoring a brain CT scan image using an ASPECTS score disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving", "resampling," "identifying," "determining," "segmenting," "computing," "recommending," and other forms thereof, are intended to be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for monitoring a brain CT scan image using an ASPECTS score. Typically, a stroke occurs when an artery in the brain ruptures and bleeds or when the blood supply to the brain is cut off. ASPECTS score may be used by a radiologist to recommend treatment to a patient. However, it is a time-consuming process for the radiologist to analyze CT scan of brain and determine ASPECTS score. More importantly, the present invention discloses a cost effective and an automatic process for analyzing the brain CT scan image. Initially, of the CT scan image of a patient is analyzed to identify a basal ganglia region and a corona radiata level. Further, a plurality of anatomical regions, a plurality of infarcts and a plurality of black regions may be segmented. Further, an overlapping region may be determined based on the plurality of anatomical regions, the plurality of infarcts, and the plurality of black regions. The overlapping region may be further used to compute an ASPECTS score. Subsequently, recommendations are generated for the patient based on the ASPECTS score.

While aspects of described system and method for monitoring a brain CT scan image using an ASPECTS score may be implemented in any number of different computing systems, environments, and/or configurations, the embodiments are described in the context of the following exemplary system.

Figure 1:
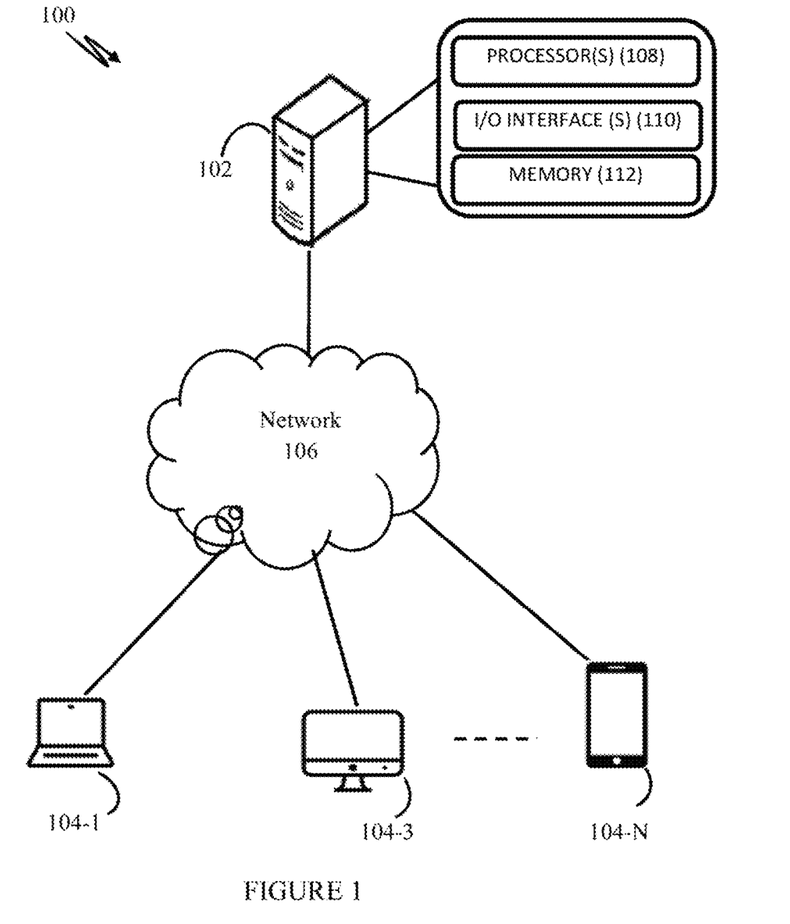
FIG. 1 illustrates a network implementation of a system for monitoring a brain CT scan image using an ASPECTS score, in accordance with an embodiment of the present subject matter.

Referring now to FIG. 1, a network implementation 100 of a system 102 for monitoring a brain CT scan image using an ASPECTS score is disclosed. It may be noted that one or more users may access the system 102 through one or more user devices 104-1, 104-2. . .104-N, collectively referred to as user devices 104, hereinafter, or applications residing on the user devices 104. In one aspect, the one or more users may comprise a doctor, a lab assistance and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1. 104-2...104-N, In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors. Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for monitoring a brain CT scan image using an ASPECTS score. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for monitoring a brain CT scan image using an ASPECTS score. The system 102 may analyze a brain NCCT (Non contrast CT) image of a patient. Further, the system 102 may identify signs of hypodensities also called infarcts, and calculate a volume of infarcts to assist a doctor on duty. In one aspect, the system 102 may highlight a region of interest on the brain NCCT image to compute an ASPECTS score. In order to compute the aspect, initially, the system 102 may receive the brain Computerized Tomography (CT) scan image of a patient. In one aspect, the brain CT scan image may provide detailed information of brain tissue and brain structures.

In one embodiment, the system 102 may check if the brain CT scan image is valid or not. In case the brain CT scan image is not valid, the system 102 may transmit a response to the user indicating that the brain CT scan image is not valid.

Further, the system 102 may resample the brain CT scan image into a plurality of slices. The brain CT scan image may be resampled using a bilinear interpolation. The bilinear interpolation may use the distance weighted average of the four nearest pixel values to estimate a new pixel value.

In one aspect, the plurality of slices may be received from a CT scanner in form of a 3D volume brain like 36 x 512 x 512. In other words, 36 slices may be received with each slice of 512 width and height.

Further, the system 102 may identify a basal ganglia region and a corona radiata level in the plurality of slices. In one aspect, the basal ganglia may indicate a group of structures found deep within cerebral hemispheres of a brain. The corona radiata may indicate a group of nerves that helps for sending and receiving messages between different regions in the brain. The basal ganglia region and the corona radiata level may be identified in a Middle Cerebral Artery (MCA) territory using a deep learning model. In one aspect, the deep learning model may comprise historical brain CT scan images, historical ASPECTS score, historical infarcts on the historical brain CT scan images, and historical anatomical regions on the historical brain CT scan images related to a set of patients.

In one embodiment, the system 102 may analyze the MCA territory on the brain CT scan image using the deep learning model. Based on the analysis, the system 102 may identify the basal ganglia region and the corona radiata level on the plurality of slices.

Subsequently, the system 102 may segment a plurality of anatomical regions upon identification of the basal ganglia region and the corona radiata level. In one embodiment, the system 102 may identify the plurality of anatomical regions on the plurality of slices. The plurality of anatomical regions may be identified using deep learning. In one aspect, a set of slices associated with the basal ganglia region and the corona radiata level may be analyzed using the deep learning. Based on the analysis, the plurality of anatomical regions may be identified.

In one embodiment, the deep learning model may be trained to identify 10 anatomical regions correctly, and find slices where the anatomical regions are found. In the embodiment, given a scan of 106 slice, the deep learning model may identify the slices where basal ganglia and corona radiata is visible. Further, the deep learning model may segment the slices into 10 regions.

In one aspect, the brain CT scan image may represent brain volume and each slice may represent a particular part of brain volume. A slice from the set of slices may have either basal ganglia or corona radiata. The identified slices may be marked with Region of Interest (ROI) anatomical regions. Each basal ganglia slice may have 7 ROI. Each corona radiata slice may have 3 ROI. The 7 ROI and 3 ROI may be marked on both half of brain. In case of the basal ganglia, 7 anatomical regions for left and 7 for right. Similarly, the corona radiata may be marked as 3 for left and 3 for right.

Once the plurality of anatomical regions is identified, the system 102 may segment the plurality of anatomical regions. The plurality of anatomical regions may be segmented using the deep learning. The plurality of anatomical regions may be segmented on the set of slices associated with the basal ganglia region and the corona radiata level. In one embodiment, once the plurality of anatomical regions is identified, the system 102 may mark the anatomical regions as segmentation mask in the set of slices which are found to be either in basal ganglia range of slice or corona radiata range of slice.

In one example, construe 10 slices of the brain CT scan image. The 10 slices may be referred as slice-1, slice-2 and the like. Further, the basal ganglia region may be identified on the slice-3, slice-4, slice-5 and slice-6. The corona radiata level may be present on slice-7 and slice-8. Furthermore, the system 102 may analyze the slice-3, slice-4, slice-5, slice-6, slice-7 and slice-8 to identify and segment the anatomical regions. In one aspect, slices related to the basal ganglia region and the corona radiata level may be consecutive.

Further, the system 102 may identify a plurality of infarcts in the plurality of slices. In one embodiment, the system 102 may analyze the plurality of slices using the deep learning. Upon analysis, the system 102 may identify the plurality of infarcts. Further, the plurality of infarcts may be segmented. In one aspect, each infarct may indicate a blockage in a blood vessel of the brain. Once the plurality of infarcts is segmented, the system 102 may mask each infarct from the plurality of infarcts.

In one embodiment, the system 102 may identify a location of each infarct and a boundary of each infarct using the deep learning. Furter, the system 102 may determine a volume of infarct using deep learning.

In one aspect, the system 102 may use meta data associated with the brain CT scan image. The meta data may be added by the CT scanner to understand resolution information of the brain CT scan image. The resolution information along with the mask predicted by the deep learning model may be used to calculate the volume of infarct. The volume of infarct may be computed using equation 1.

Volume=Slice_resolution_x*slice resolution_y*slice_resolution_z *(pixel present in mask). . . Equation 1

Wherein,
Slice_resolution_x indicates a resolution of x slice;
Slice_resolution_y indicates a resolution of y slice;
Slice_resolution_z indicates a resolution of z slice; and
pixel present in mask indicate pixels of the mask.

Subsequently, the system 102 may analyze the plurality of slices to extract a white matter region and a grey matter region. In an aspect, the plurality of slices may be analyzed using a windowing technique. In an aspect, the windowing technique may be referred as a Hu windowing technique. In one embodiment, the system 102 may use the deep learning model to extract the white matter region and the grey matter region. The system 102 may train the deep learning model using the historical brain CT scan images, and white and grey regions associated with the historical brain CT scan images.

Upon extraction, the system 102 may perform a fast Fourier transform technique on the plurality of slices. Further, the system 102 may determine a density of the white matter region and a density of the grey matter region on each of the plurality of slices. In an aspect, the density of the white matter region and the density of the grey matter region may be equal or different.

In one embodiment, if the density of the white matter region and the density of the grey matter region is equal to a threshold density, a plurality of white regions may be present in the plurality of slices. In another embodiment, if the density of the white matter region and the density of the grey matter region is less than the threshold density, a plurality of black regions may be present in the plurality of slices. In one example, the plurality of black regions may correspond to a lack of grey and white matter regions. The system 102 may further segment the plurality of black regions in the plurality of slices. The black regions may indicate a defect associated with the brain, Once the plurality of black regions is segmented, the system 102 may mask the plurality of black regions.

In an aspect, the system 102 may use the deep learning model to segment the plurality of black regions. The system 102 may train the deep learning model using the historical brain CT scan images and historical black regions associated with the historical brain CT scan images. The deep learning model may analyze the plurality of slices to identify the change in the density of the whitter matter region and the grey matter region. Based on the analysis, the system 102 may identity the plurality of black regions in the plurality of slices.

Figure 3:
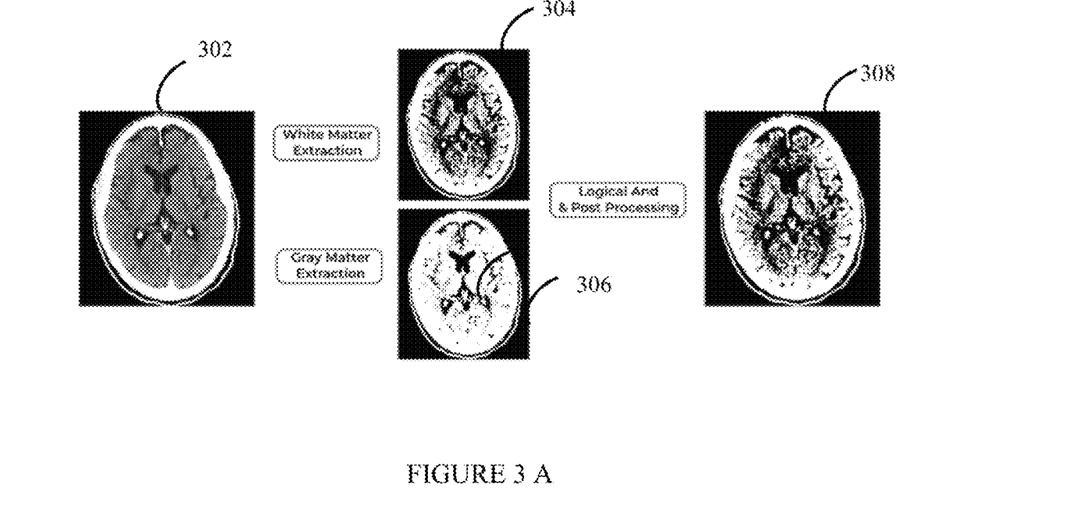
FIG. 3A illustrates a segmentation of a plurality of black regions, in accordance with an embodiment of the present subject matter.
FIG. 3B shows a contra-lateral comparison used for the segmentation of the plurality of black regions, in accordance with an embodiment of the present subject matter.

Referring now to FIG. 3A, a segmentation of a plurality of black regions is shown, in accordance with an embodiment of the present subject matter. In one embodiment, the brain CT scan image 302 may be received. Further, the system 102 may extract the white matter region 304 and the grey matter region 306 by analysis of the brain CT scan image 302. Further, the Fourier transform technique may be used to analyze the white matter region 304 and the grey matter region 306. Based on the analysis, the plurality of black regions may be identified in the brain CT scan image at 308.

Referring again to FIG. 1, the system 102 may further determine an overlapping region across the plurality of slices. The overlapping region may be determined based on the plurality of anatomical regions, the plurality of infarcts, and the plurality of black regions, in one aspect, the plurality of anatomical regions may be overlayed with the plurality of infarcts. In another aspect, the plurality of anatomical regions may be overlayed with the plurality of black regions. Further, common area covered by the anatomical region and the infarct, and the anatomical region and the black region may be identified. The common area may be referred as the overlapping region. The overlapping region may indicate an affected area of the brain in the brain CT scan image. In other words, the overlapping region may indicate the affected area in the scan image from MCA region of brain that contains basal ganglia and corona radiata level.

In one embodiment, once the plurality of black regions is overlayed on the plurality of anatomical regions, the overlapping region on a left portion and a right portion of the brain CT scan may be identified. Further, the system 102 may perform a contra-lateral comparison between the overlapping region on the left portion and the right portion of the brain in the brain CT scan image. Based on performing the contra-lateral comparison, the system 102 may accurately identify the affected areas associated with the plurality of black regions. In an aspect, the contra-lateral comparison may indicate comparing corresponding ASPECTS relevant MCA regions on the left portion and the right portion against each other with baseline point estimates on HU value like mean, standard deviation and 90th percentile. In one aspect, the system 102 may be configured to perform comparison between caudate left and caudate right area of the brain, and check for decrease in density of grey and white matter, the black region produced by the technique will correspond to loss of density of both grey and white matter.

Referring now to FIG. 3B, a contra-lateral comparison used for segmentation of a plurality of slices is shown, in accordance with an embodiment of the present subject matter. In one embodiment, the plurality of anatomical regions may be overlayed on the plurality of black regions. Further, the overlapping regions associated with the left portion 310 and the right portion 312 may be analyzed using the contra-lateral comparison. Further, the affected areas corresponding to the plurality of black regions may be identified in the brain CT scan imaged based on the analysis.

Referring again to FIG. 1, once the overlapping region computing, the system 102 may compute an Alberta stroke programme early CT score (ASPECTS) score based on the overlapping region and a predefined threshold. The system 102 may deduct a defined point from the predefined threshold when the overlapping region is determined. In one example, for each overlying of the anatomical region and the infarct, one point may be deducted from the predefined threshold. In the example, for each overlaying of the anatomical region and the black region, one point may be deducted from the predefined threshold. Upon deduction, the system 102 may compute the ASPECTS score. In one aspect, the ASPECTS score may be further used to determine a severity of a brain stroke. In one embodiment, the ASPECTS score may be generated using an artificial intelligence technique. In one embodiment, the ASPECTS score may indicate potential strokes of the patient.

In one example, construe 3 overlapping regions may be determined. The predefined threshold may be 10. The defined point that may be deducted is 1. Further, the system 102 may deduct 3 points from the predefined threshold i.e., 10. Thus, the ASPECTS score may be 7.

In one aspect, the ASPECTS score may help the doctor to identify areas of irreversible injury in the brain CT scan image. The areas of injury may be identified using an image registration technique.

Once the ASPECTS score is computed, the system 102 may recommend a course of action to the patient. The course of action may be recommended based on the ASPECTS score and a predefined ASPECTS score. In one aspect, the ASPECTS score may be compared with the predefined ASPECTS score. If the ASPECTS score is greater than the predefined ASPECTS score, then the severity of the brain stroke may be less. If the ASPECTS score is less than or equal to the predefined ASPECTS score, then the severity of the brain stroke may be high. Based on the comparison, the system 102 may recommend the course of action to the patient in real-time. The course of action may comprise medication for the patient, further scans and the like.

In one embodiment, the system 102 may segment an area score for infarct and label the infarct with a biological name. Further, for infarct segmentation model, the system 102 may use the mask and fit the mask over a template having the ATLAS of brain to find the name for the region having infarct. In one aspect, ATLAS means a template brain that may be annotated for different regions which exists in the brain.

In one embodiment, the volume of the infarct and the ASPECTS score may help the doctor to take decision on either recommend a specialist or prioritize the patient for surgery like thrombectomy or drug treatment like thrombolysis.

In one embodiment, the system 102 may be configured to detect stroke from the brain CT scan image. The system 102 may further help to prioritize patient's having stroke in busy hospitals.

Figure 2:
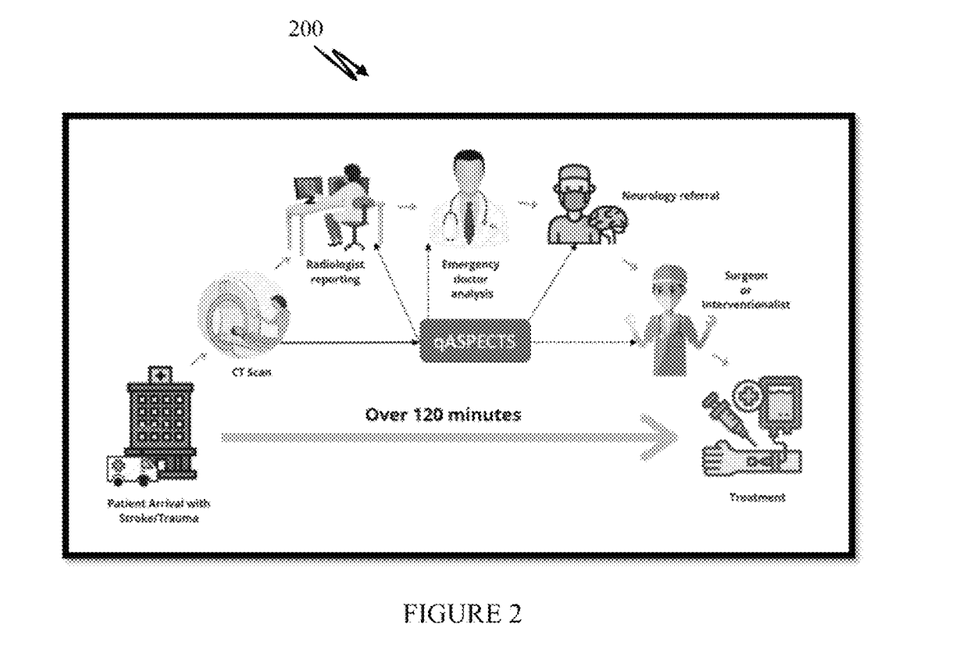
FIG. 2 illustrates an exemplary embodiment of the system for monitoring a brain CT scan image using an ASPECTS score, in accordance with an embodiment of the present subject matter.

Referring now to FIG. 2, an exemplary embodiment 200 of the system for monitoring a brain CT scan image using an ASPECTS score is shown in accordance with an embodiment of the present subject matter. In one embodiment, construe a patient arrived at a hospital. The patient may have suffered from a brain stroke. Further, the patient may be advised to go for a brain CT scan. The brain CT scan may be further fed to the system 102. The system 102 may be referred as a qASPECTS system.

The system 102 may identify a basal ganglia region and a corona radiata level by analyzing the brain CT scan image. Further, the system 102 may segment a plurality of anatomical regions upon identification of the basal ganglia region and the corona radiata level. Furthermore, the system 102 may segment a plurality of infarcts in the plurality of slices using deep learning. Subsequently, the system 102 may segment the plurality of black regions in the plurality of slices. The plurality of anatomical regions, the plurality of infarcts, and the plurality of black regions may be used to determine an overlapping region. The overlapping region and a predefined threshold may be used to compute an ASPECTS score. Once the ASPECTS score is determined, the system may provide recommendations to the patient or to a doctor of the patient. The recommendation may comprise a treatment for the patient or the medication for the patient.

In one embodiment, the system 102 may help the doctor or a radiologist to take proper decision of the treatment for the patient. The system may reduce a usual time required for an analysis of the brain CT scan.

Figure 4:
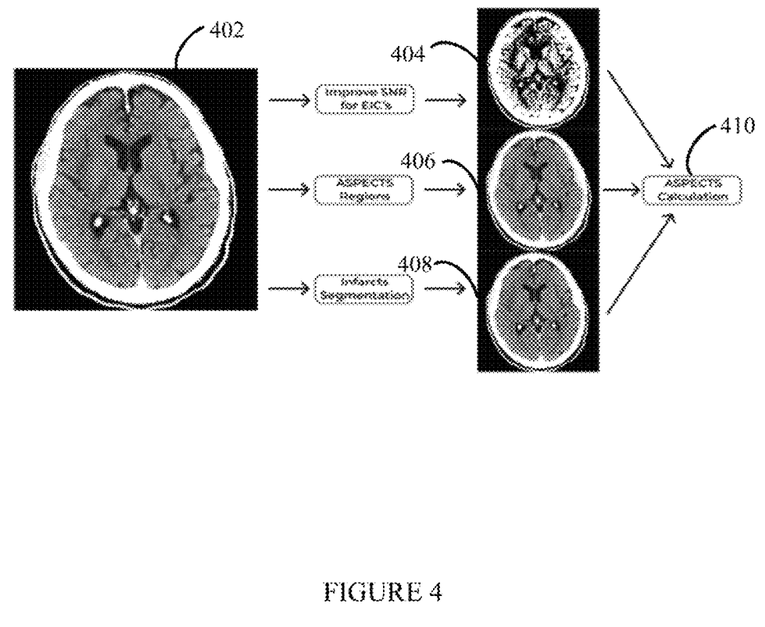
FIG. 4 illustrates a block diagram for determination of an aspect score, in accordance with an embodiment of the present subject matter.

Referring now to FIG. 4, a block diagram 400 for determination of an aspect score is disclosed, in accordance with an embodiment of the present subject matter. In one embodiment, Non contrast CT (NCCT) scan 402 of a brain of a patient may be received. Further, at block 406, anatomical regions may be identified in the NCCT scan. Furthermore, at block 408, infracts may be identified. Subsequently, at block 404, black regions may be identified in the NCCT scan. In an aspect, the infracts may be overlayed on the anatomical regions, and the black regions may be overlayed on the anatomical regions. Upon overlaying, a location and a number of the infarcts and the black regions may be determined. Further, at block 410, an ASPECTS score may be computed based on the number of the infarcts and the black regions. In one example, for each infarct and the black region, 2 points may be deducted from a standard aspect score i.e., 10. The ASPECTS score may be based on the anatomical regions, the infarcts, and the black. regions.

Figure 5:
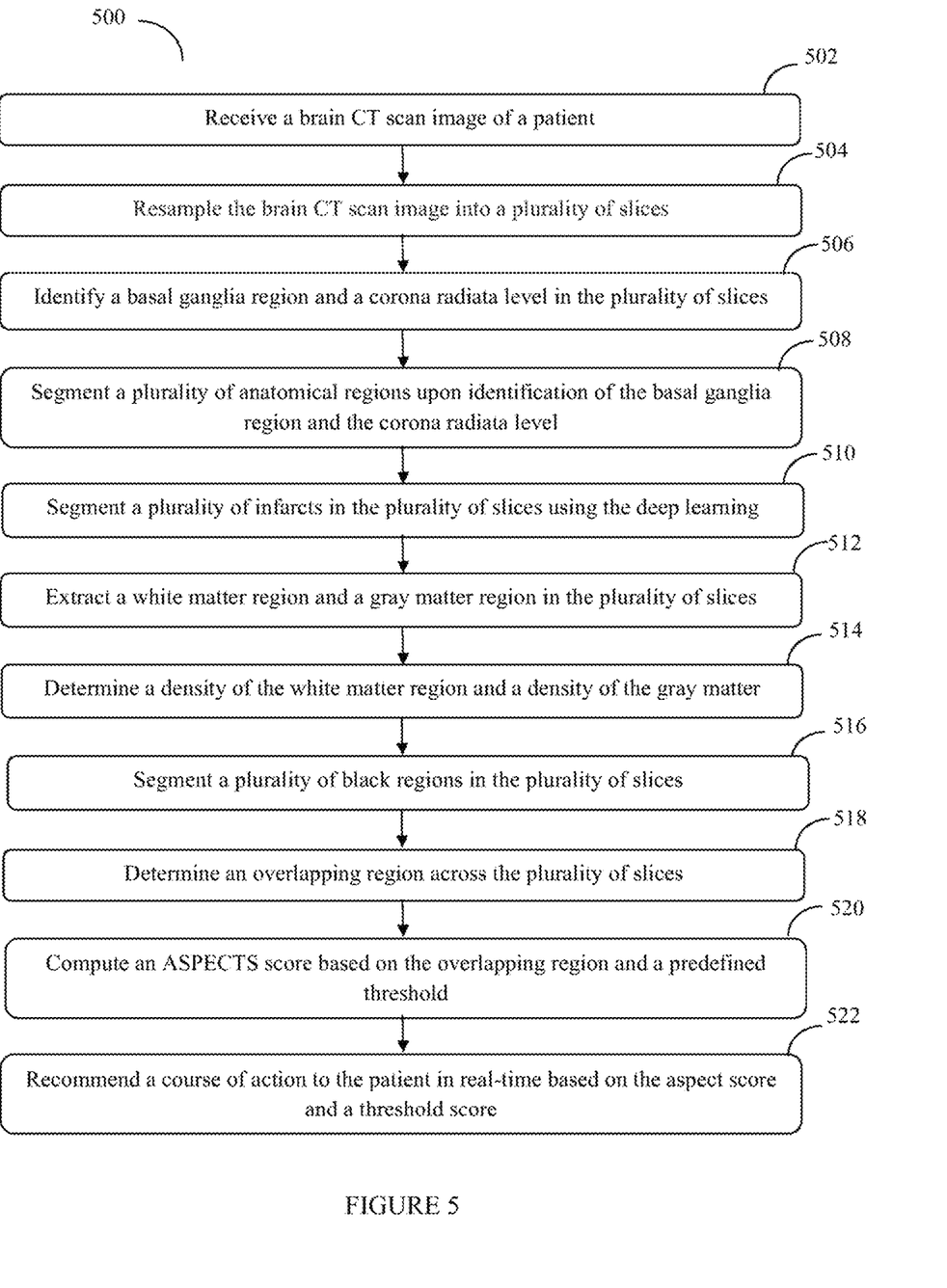
FIG. 5 illustrates a method for monitoring a brain CT scan image using an ASPECTS score, in accordance with an embodiment of the present subject matter.

Referring now to FIG. 5, a method 500 for monitoring a brain CT scan image using an ASPECTS score is shown, in accordance with an embodiment of the present subject matter. The method 500 may be described in the general context of computer executable instructions. Generally, computer executable instructions can include routines, programs, objects, components, data structures, procedures, modules, functions, etc., that perform particular functions or implement particular abstract data types.

The order in which the method 500 is described is not intended to be construed as a limitation, and any number of the described method blocks can be combined in any order to implement the method 500 or alternate methods for monitoring a brain CT scan image using an ASPECTS score. Additionally, individual blocks may be deleted from the method 500 without departing from the spirit and scope of the subject matter described herein. Furthermore, the method 500 for monitoring a brain CT scan image using an ASPECTS score can be implemented in any suitable hardware, software, firmware, or combination thereof. However, for ease of explanation, in the embodiments described below, the method 500 may be considered to be implemented in the above described system 102.

At block 502, a brain CT scan image of a patient may be received.

At block 504, the brain CT scan image may be resampled into a plurality of slices. In an aspect, the brain CT scan image may be resampled using a bilinear interpolation.

At block 506, a basal ganglia region and a corona radiata level in the plurality of slices may be identified. In an aspect, the basal ganglia region and the corona radiata level may be identified in a Middle Cerebral Artery (MCA) territory using a deep learning model.

At block 508, a plurality of anatomical regions may be segmented upon identification of the basal ganglia region and the corona radiata level. In an aspect, the plurality of anatomical regions may be segmented using deep learning. The plurality of anatomical regions may be segmented on a set of slices associated with the basal ganglia region and the corona radiata level.

At block 510, a plurality of infarcts in the plurality of slices may be segmented using the deep learning.

At block 512, a white matter region and a grey matter region in the plurality of slices may be extracted using a windowing technique.

At block 514, a density of the white matter region and a density of the grey matter region may be determined based on an analysis of the plurality of slices using a fast Fourier transform technique.

At block 516, a plurality of black regions in the plurality of slices may be segmented based on comparison of the e density of the white matter region and the grey matter region with a threshold density.

At block 518, an overlapping region across the plurality of slices may be determined. In an aspect, the overlapping region may be determined based on the plurality of anatomical regions, the plurality of infarcts and the plurality of black regions. The overlapping region may indicate an affected area of brain in the brain CT scan image.

At block 520, an ASPECTS score may be computed based on the overlapping region and a predefined threshold. In an aspect, a defined point may he deducted from the predefined threshold when the overlapping region is determined.

At block 522, a course of action to the patient may be recommended in real-time based on the ASPECTS score and a threshold score, thereby monitoring a brain CT scan image.

Exemplary embodiments discussed above may provide certain advantages. Though not required to practice aspects of the disclosure, these advantages may include those provided by the following features.

Some embodiments of the system and the method enable alerting a doctor regarding potential.

Some embodiments of the system and the method enable assisting the doctor to provide proper medication to the patient in real-time based on analyzing a brain CT scan.

Some embodiments of the system and the method enable analyzing a brain CT scan image of a patient using deep learning.

Some embodiments of the system and the method enable segmenting anatomical regions and infarcts using deep learning.

Some embodiments of the system and the method enable increasing a signal to noise ratio by identifying a plurality of black regions that indicates a defect in the brain CT scan image.

Although implementations for methods and system for monitoring a brain CT scan image using an ASPECTS score have been described in language specific to structural features and/or methods, it is to be understood that the appended claims are not necessarily limited to the specific features or methods described. Rather, the specific features and methods are disclosed as examples of implementations for monitoring the CT scan image using an ASPECTS score.

We claim:

1. A method to monitor a brain CT scan image, the method comprises:
   receiving, by a processor, a brain CT scan image of a patient;
   resampling, by the processor, the brain CT scan image into a plurality of slices, wherein the brain CT scan image is resampled using a bilinear interpolation;
   identifying, by the processor, a basal ganglia region and a corona radiata level in the plurality of slices, wherein the basal ganglia region and the corona radiata level are identified in a Middle Cerebral Artery (MCA) territory using a deep learning model;
   segmenting, by the processor, a plurality of anatomical regions upon identification of the basal ganglia region and the corona radiata level, wherein the plurality of anatomical regions is segmented using deep learning, and wherein the plurality of anatomical regions is segmented on a set of slices associated with the basal ganglia region and the corona radiata level;
   segmenting, by the processor, a plurality of infarcts in the plurality of slices using the deep learning;
   extracting, by the processor, a white matter region and a grey matter region in the plurality of slices using a windowing technique;
   determining, by the processor, a density of the white matter region and a density of the grey matter region on each of the plurality of slices based on an analysis of the plurality of slices using a fast Fourier transform technique;
   segmenting, by the processor, a plurality of black regions in the plurality of slices based on comparison of the density of the white matter region and the grey matter region with a threshold density;
   determining, by the processor, an overlapping region across the plurality of slices, wherein the overlapping region is determined based on the plurality of anatomical regions, the plurality of infarrcts and the plurality of black regions, and wherein the overlapping region indicates an affected area of brain in the brain CT scan image;
   computing, by the processor, an ASPECTS score based on the overlapping region and a predefined threshold, wherein a defined point is deducted from the predefined threshold when the overlapping region is determined; and recommending, by the processor, a course of action to the patient in real-time based on the ASPECTS score and a threshold score, thereby monitoring a brain CT scan image.

2. The method as claimed in claim 1, comprises overlaying the plurality of anatomical regions and the plurality of black regions to identify the overlapping region, wherein the overlapping region on a left portion and a right portion of the brain CT scan image is compared using a contra-lateral comparison technique.

3. The method as claimed in claim 1 comprises identifying a location of each infarct and a boundary of each infarct using the deep learning.

4. The method as claimed in claim 1 comprises determining a volume of infarct using deep learning.

5. The method as claimed in claim 1 comprises masking the plurality of anatomical regions on the set of slices, and the plurality of infarcts on the plurality of slices.

6. The method as claimed in claim 1, wherein the deep learning model comprise historical brain CT scan images, historical ASPECTS score, historical infarcts on the historical brain CT scan images, and historical anatomical regions on the historical brain CT scan images related to a set of patients.

7. A system to monitor a brain CT scan image, the system comprises;
a memory;
a processor coupled to the memory, wherein the processor is configured to execute a set of instructions stored in the memory to:
receive a brain CT scan image of a patient;
resample the brain CT scan image into a plurality of slices, wherein the brain CT scan image is resampled using a bilinear interpolation;
identify a basal ganglia region and a corona radiata level in the plurality of slices, wherein the basal ganglia region and the corona radiata level are identified in a Middle Cerebral Artery (MCA) territory using a deep learning model;
segment a plurality of anatomical regions upon identification of the basal ganglia region and the corona radiata level, wherein the plurality of anatomical regions is segmented using deep learning, and wherein the plurality of anatomical regions is segmented on a set of slices associated with the basal ganglia region and the corona radiata level;
segment a plurality of infarcts in the plurality of slices using the deep learning;
extract a white matter region and a grey matter region in the plurality of slices using a windowing technique;
determine a density of the white matter region and a density of the grey matter region on each of the plurality of slices based on an analysis of the plurality of slices using a fast Fourier transform technique;
segment a plurality of black regions in the plurality of slices based on comparison of the density of the white matter region and the grey matter region with a threshold density;
determine an overlapping region across the plurality of slices, wherein the overlapping region is determined based on the plurality of anatomical regions, the plurality of infarcts and the plurality of black regions, and wherein the overlapping region indicates an affected area of brain in the brain CT scan image;
compute an ASPECTS score based on the overlapping region and a predefined threshold, wherein a defined point is deducted from the predefined threshold when the overlapping region is determined; and
recommend a course of action to the patient in real-time based on the ASPECTS score and a threshold score, thereby monitoring a brain CT scan image.

8. The system as claimed in claim 7, comprises overlaying the plurality of anatomical regions and the plurality of black regions to identify the overlapping region, Wherein the overlapping region on a left portion and a right portion of the brain CT scan image is compared using a contra-lateral comparison technique.

9. The system as claimed in claim 7, comprises identifying a location of each infarct and a boundary of each infarct using the deep learning.

10. The system as claimed in claim 7, comprises determining a volume of infarct using deep learning.

11. The system as claimed in claim 7, comprises masking the plurality of anatomical regions on the set of slices, and the plurality of infarcts on the plurality of slices.

12. The system as claimed in claim 7, wherein the deep learning model comprise historical brain CT scan images, historical ASPECTS score, historical infarcts on the historical brain CT scan images, and historical anatomical regions on the historical brain CT scan images related to a set of patients.

13. A non-transitory computer program product having embodied thereon a computer program for monitoring a brain CT scan image, the computer program product storing instructions, the instructions comprising instructions for:
receiving a brain CT scan image of a patient;
resampling the brain CT scan image into a plurality of slices, wherein the brain CT scan image is resampled using a bilinear interpolation;
identifying a basal ganglia region and a corona radiata level in the plurality of slices, wherein the basal ganglia region and the corona radiata level are identified in a Middle Cerebral Artery (MCA) territory using a deep learning model;
segmenting a plurality of anatomical regions upon identification of the basal ganglia region and the corona radiata level, wherein the plurality of anatomical regions is segmented using deep learning, and wherein the plurality of anatomical regions is segmented on a set of slices associated with the basal ganglia region and the corona radiata level;
segmenting a plurality of infarcts in the plurality of slices using the deep learning;
extracting a white matter region and a grey matter region in the plurality of slices using a windowing technique;
determining a density of the white matter region and a density of the grey matter region on each of the plurality of slices based on an analysis of the plurality of slices using a fast Fourier transform technique;
segmenting a plurality of black regions in the plurality of slices based on comparison of the density of the white matter region and the grey matter region with a threshold density;
determining an overlapping region across the plurality of slices, wherein the overlapping region is determined based on the plurality of anatomical regions, the plurality of infarcts and the plurality of black regions, and wherein the overlapping region indicates an affected area of brain in the brain CT scan image;
computing an ASPECTS score based on the overlapping region and a predefined threshold, wherein a defined point is deducted from the predefined threshold when the overlapping region is determined; and recommending a course of action to the patient in real-time based on the ASPECTS score and a threshold score, thereby monitoring a brain CT scan image.

* * * * *